United States Patent
Williams et al.

(10) Patent No.: US 11,553,921 B2
(45) Date of Patent: Jan. 17, 2023

(54) SURGICAL STAPLING DEVICE WITH FLEXIBLE SHAFT

(71) Applicant: Covidien LP, Mansfield, MA (US)

(72) Inventors: Justin Williams, Southbury, CT (US); Russell Pribanic, Roxbury, CT (US); David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 66 days.

(21) Appl. No.: 17/328,047

(22) Filed: May 24, 2021

(65) Prior Publication Data

US 2022/0015767 A1 Jan. 20, 2022

Related U.S. Application Data

(60) Provisional application No. 63/052,006, filed on Jul. 15, 2020.

(51) Int. Cl.
*A61B 17/064* (2006.01)
*A61B 17/115* (2006.01)
*A61B 17/00* (2006.01)
*A61B 17/072* (2006.01)

(52) U.S. Cl.
CPC ... *A61B 17/1155* (2013.01); *A61B 2017/0046* (2013.01); *A61B 2017/00367* (2013.01); *A61B 2017/00862* (2013.01); *A61B 2017/07257* (2013.01); *A61B 2017/07285* (2013.01)

(58) Field of Classification Search
CPC .................. A61B 17/1155; A61B 2017/00367
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Jan. 11, 2022, issued in corresponding EP Appln. No. 21185496, 11 pages.

*Primary Examiner* — Eyamindae C Jallow
(74) *Attorney, Agent, or Firm* — Carter, DeLuca & Farrell LLP (57) ABSTRACT

A circular stapling device includes an elongate body having a flexible outer tube that supports a reload assembly, a flexible inner cable that supports an anvil assembly, and a flexible central tube that is supported about the inner cable and within the outer tube. The stapling device is configured to access body cavities which cannot be easily accessed by a circular stapling device having a rigid shaft.

20 Claims, 8 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A * | 9/1991 | Avant .................. A61B 17/115 606/153 |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A * | 3/1993 | Bessler ................ A61B 17/115 600/129 |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant .................. A61B 17/115 227/19 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A * | 9/1994 | Blanco .................. F16M 11/40 403/56 |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |

(56) References Cited

U.S. PATENT DOCUMENTS

| | | |
|---|---|---|
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,667,805 B1 * | 6/2020 | Bourland, III ... A61B 17/06066 |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253367 A1 * | 10/2012 | Yamakawa ............ A61B 17/11 606/153 |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |

(56) References Cited

U.S. PATENT DOCUMENTS

| | | | |
|---|---|---|---|
| 2015/0209045 A1 | 7/2015 | Hodgkinson et al. | |
| 2019/0255285 A1* | 8/2019 | Freeseman | A61M 25/0084 |
| 2019/0314013 A1* | 10/2019 | Whitman | A61B 17/1155 |

FOREIGN PATENT DOCUMENTS

| | | | |
|---|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004032766 A2 | 4/2004 |
| WO | 2004047654 A2 | 6/2004 |
| WO | 2008107918 A1 | 9/2008 |

\* cited by examiner

SURGICAL STAPLING DEVICE WITH FLEXIBLE SHAFT

CROSS-REFERENCE TO RELATED APPLICATIONS

This application claims the benefit of and priority to U.S. Provisional Patent Application No. 63/052,006, filed Jul. 15, 2020, the entire contents of which is incorporated by reference herein.

FIELD

This disclosure is directed to stapling devices and, more particularly, to endoscopic stapling devices with flexible shafts that support an end effector.

BACKGROUND

Surgical stapling devices for performing surgical procedures endoscopically are well known and are commonly used to reduce patient trauma and shorten patient recovery times. Typically, an endoscopic stapling device includes a handle assembly, a rigid elongate body that extends distally from the handle assembly, and an end effector including a tool assembly that is supported on a distal portion of the elongate body. The handle assembly is coupled to the end effector by drive mechanisms that extend through the elongate body such that a clinician can control operation of the end effector remotely via the handle assembly.

Surgical stapling devices for endoscopic use are available in a variety of configurations including linear and circular. Circular stapling devices are commonly used to perform end to end anastomoses after resections of the large bowel, i.e., colectomies. In a large percentage of colectomy procedures, the portion of the colon that must be resected is in the ascending colon or the transverse colon which cannot be easily accessed by a circular stapling device having a rigid shaft. As such, these procedures are typically performed during an open colectomy procedure which result in increased patient trauma and recovery time.

A continuing need exists in the medical arts for a stapling device of minimal complexity having a flexible shaft for accessing a surgical site.

SUMMARY

Aspects of the disclosure are directed to a surgical stapling device including an elongate body that supports a tool assembly. The elongate body is flexible and includes a flexible outer tube, a flexible central tube, and an inner cable. The flexible elongate body allows the tool assembly to access surgical sites deep within a body cavity.

One aspect of the disclosure is directed to a circular stapling device that includes a handle assembly, an elongate body, and a tool assembly including a reload assembly and an anvil assembly. The elongate body includes a flexible outer tube, a flexible central tube, and a flexible inner cable. The flexible outer tube has a proximal portion fixedly coupled to a body of the reload assembly and a distal portion that is coupled to a stationary handle of the handle assembly. The flexible central tube has a distal portion that is coupled to the reload assembly and a proximal portion that is coupled to a trigger of the handle assembly. The inner cable has a distal portion that is coupled to an anvil assembly of the tool assembly and a proximal portion that is coupled to a rotation knob of the handle assembly. The stapling device is configured to access body cavities which cannot be easily accessed by a circular stapling device having a rigid shaft.

Another aspect of this disclosure is directed to a surgical stapling device including a handle assembly, an elongate body, and a tool assembly. The handle assembly includes a stationary handle, a trigger coupled to the stationary handle, and a rotation knob. The elongate body includes a flexible outer tube, a flexible central tube, and a flexible inner cable. The flexible outer tube has a proximal portion and a distal portion. The proximal portion of the flexible outer tube is fixedly coupled to the stationary handle of the handle assembly. The flexible central tube has a proximal portion and a distal portion and is movable within the flexible outer tube between retracted and advanced positions. The proximal portion of the flexible central tube is coupled to the trigger of the handle assembly such that actuation of the trigger causes movement of the flexible central tube between its retracted and advanced positions. The flexible inner cable is movable within the central tube between advanced and retracted positions and includes a proximal portion and a distal portion. The distal portion of the flexible inner cable supports an anvil retainer. The proximal portion of the flexible inner cable is coupled to the rotation knob such that rotation of the rotation knob in relation to the stationary housing of the handle assembly causes movement of the flexible inner cable between its retracted and its advanced positions. The tool assembly includes a reload assembly that is supported on the distal portion of the outer tube and includes a body supporting a staple cartridge having staples. The anvil assembly is coupled to the anvil retainer and is movable in relation to the staple cartridge between spaced and clamped positions in response to movement of the flexible inner cable between its advanced and retracted positions.

In aspects of the disclosure, the anvil retainer includes a trocar and the anvil assembly is adapted to be releasably coupled to the trocar.

In some aspects of the disclosure, the distal portion of the flexible outer tube is coupled to the body of the reload assembly by a rigid connector that defines a cavity.

In certain aspects of the disclosure, the distal portion of the flexible central tube includes a rigid drive member that is movable within the cavity of the connector between retracted and advanced positions in response to movement of the flexible central tube between its retracted and advanced positions.

In aspects of the disclosure, the reload assembly includes a pusher assembly that is movable from a retracted position to an advanced position in response to movement of the drive member from its retracted to its advanced position to eject the staples from the staple cartridge.

In some aspects of the disclosure, the reload assembly includes a knife assembly having an annular knife blade.

In certain aspects of the disclosure, the knife assembly is movable from a retracted position to an advanced position in response to movement of the drive member from its retracted position to its advanced position to advance the annular knife blade through the staple cartridge.

In aspects of the disclosure, the proximal portion of the central tube supports a rigid coupling member that is coupled to the trigger by a pivot member.

In some aspects of the disclosure, the reload assembly is releasably coupled to the body of the reload assembly by a coupling mechanism.

In certain aspects of the disclosure, the flexible central tube is formed from coil pipe.

In aspects of the disclosure, the inner cable is formed from wire rope.

In aspects of the disclosure, the outer tube is formed from nylon plastic flexible tubing.

In aspects of the disclosure, the inner cable is formed from wire rope, the flexible central tube is formed from coil pipe, and the outer tube is formed from flexible tubing.

Other aspects of the disclosure are directed to a surgical stapling device including a handle assembly, an elongate body, and a tool assembly. The handle assembly includes a stationary handle, a trigger coupled to the stationary handle, and a rotation knob. The elongate body includes a flexible outer tube, a flexible central tube, and a flexible inner cable. The flexible outer tube has a proximal portion and a distal portion. The proximal portion of the flexible outer tube is fixedly coupled to the stationary handle of the handle assembly. The flexible central tube has a proximal portion and a distal portion and is movable within the flexible outer tube between retracted and advanced positions. The proximal portion of the flexible central tube is coupled to the trigger of the handle assembly such that actuation of the trigger causes movement of the flexible central tube between its retracted and advanced positions. The flexible inner cable is movable within the central tube between retracted and advanced positions and includes a proximal portion and a distal portion. The distal portion of the flexible inner cable supports an anvil retainer. The proximal portion of the flexible inner cable is coupled to the rotation knob such that rotation of the rotation knob in relation to the stationary housing of the handle assembly causes movement of the flexible inner cable between its retracted and its advanced positions. The tool assembly includes a reload assembly and an anvil assembly. The reload assembly is supported on the distal portion of the outer tube and includes a body that supports a staple cartridge having staples. The anvil assembly is coupled to the anvil retainer and is movable in relation to the staple cartridge between spaced and clamped positions in response to movement of the flexible inner cable between its advanced and retracted positions. The rigid connector defines a cavity that connects the flexible outer tube to the body of the reload assembly and defines a cavity. The rigid drive member is supported on the distal portion of the flexible central tube and is movable within the cavity of the connector between retracted and advanced positions in response to movement of the flexible central tube between its retracted and advanced positions.

Yet another aspect of the disclosure is directed to a surgical stapling device including a handle assembly, an elongate body, and a tool assembly. The handle assembly includes a stationary handle, a trigger coupled to the stationary handle, and a rotation knob. The elongate body includes an outer tube formed of flexible tubing, a central tube formed of coil pipe, and an inner cable formed of wire rope. The outer tube has a proximal portion and a distal portion. The proximal portion of the outer tube is fixedly coupled to the stationary handle of the handle assembly. The central tube has a proximal portion and a distal portion and is movable within the outer tube between retracted and advanced positions. The proximal portion of the central tube is coupled to the trigger of the handle assembly such that actuation of the trigger causes movement of the central tube between its retracted and advanced positions. The inner cable is movable within the central tube between retracted and advanced positions and includes a proximal portion and a distal portion that supports an anvil retainer. The proximal portion of the inner cable is coupled to the rotation knob such that rotation of the rotation knob in relation to the stationary housing of the handle assembly causes movement of the inner cable between its retracted and its advanced positions. The tool assembly includes a reload assembly and an anvil assembly. The reload assembly is supported on the distal portion of the outer tube and includes a body supporting a staple cartridge having staples. The anvil assembly is coupled to the anvil retainer and is movable in relation to the staple cartridge between spaced and clamped positions in response to movement of the inner cable between its advanced and retracted positions.

Other aspects of the disclosure will be appreciated from the following description.

BRIEF DESCRIPTION OF THE DRAWINGS

Various exemplary aspects of the disclosed surgical stapling device are described herein below with reference to the drawings, wherein.

DETAILED DESCRIPTION

The disclosed surgical stapling device will now be described in detail with reference to the drawings in which like reference numerals designate identical or corresponding elements in each of the several views. However, it is to be understood that the aspects of the disclosure described herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 1:
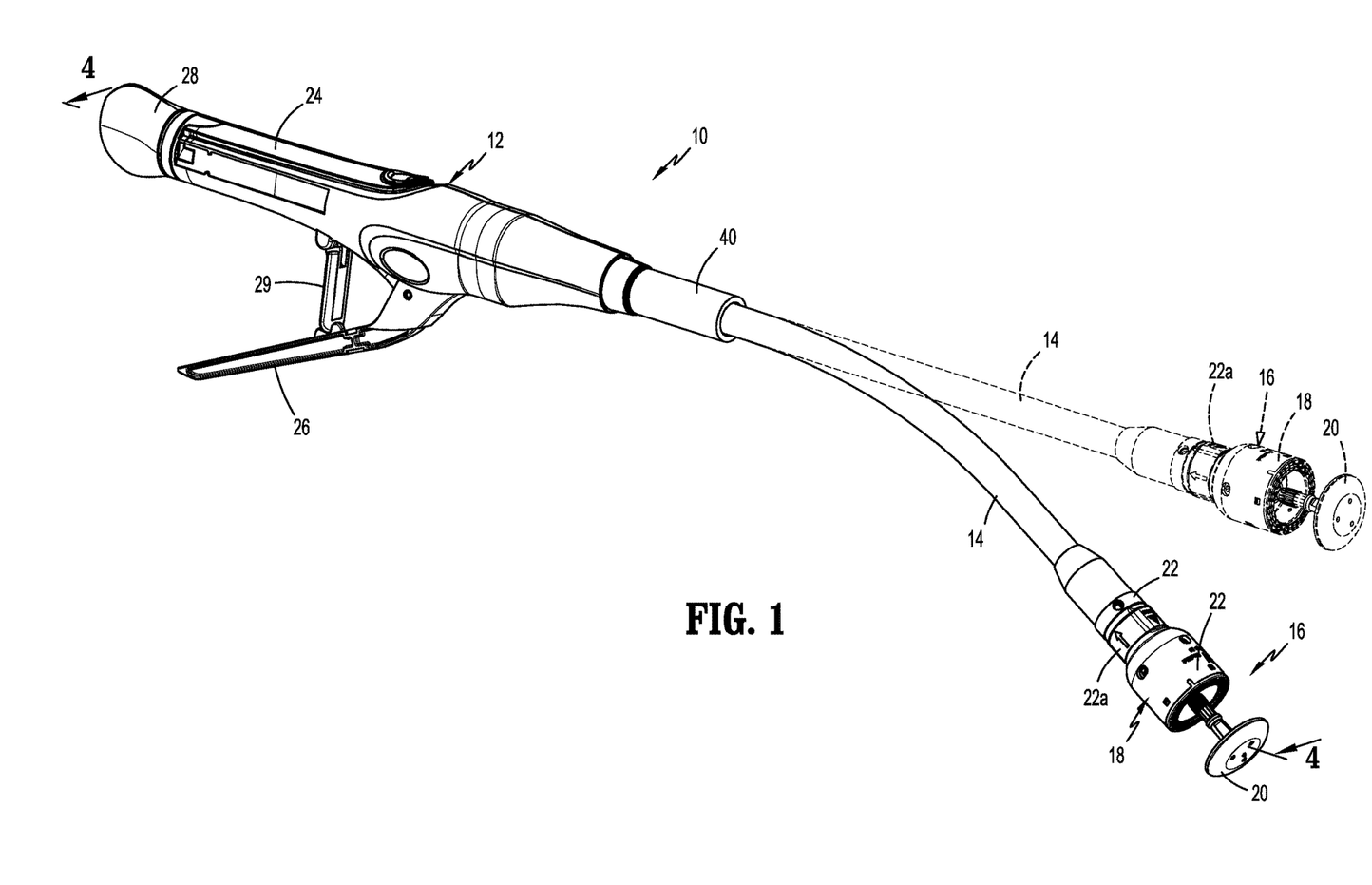
FIG. 1 is a side perspective view of a surgical stapling device in accordance with aspects of the disclosure with a tool assembly in an open position.
Figure 4:
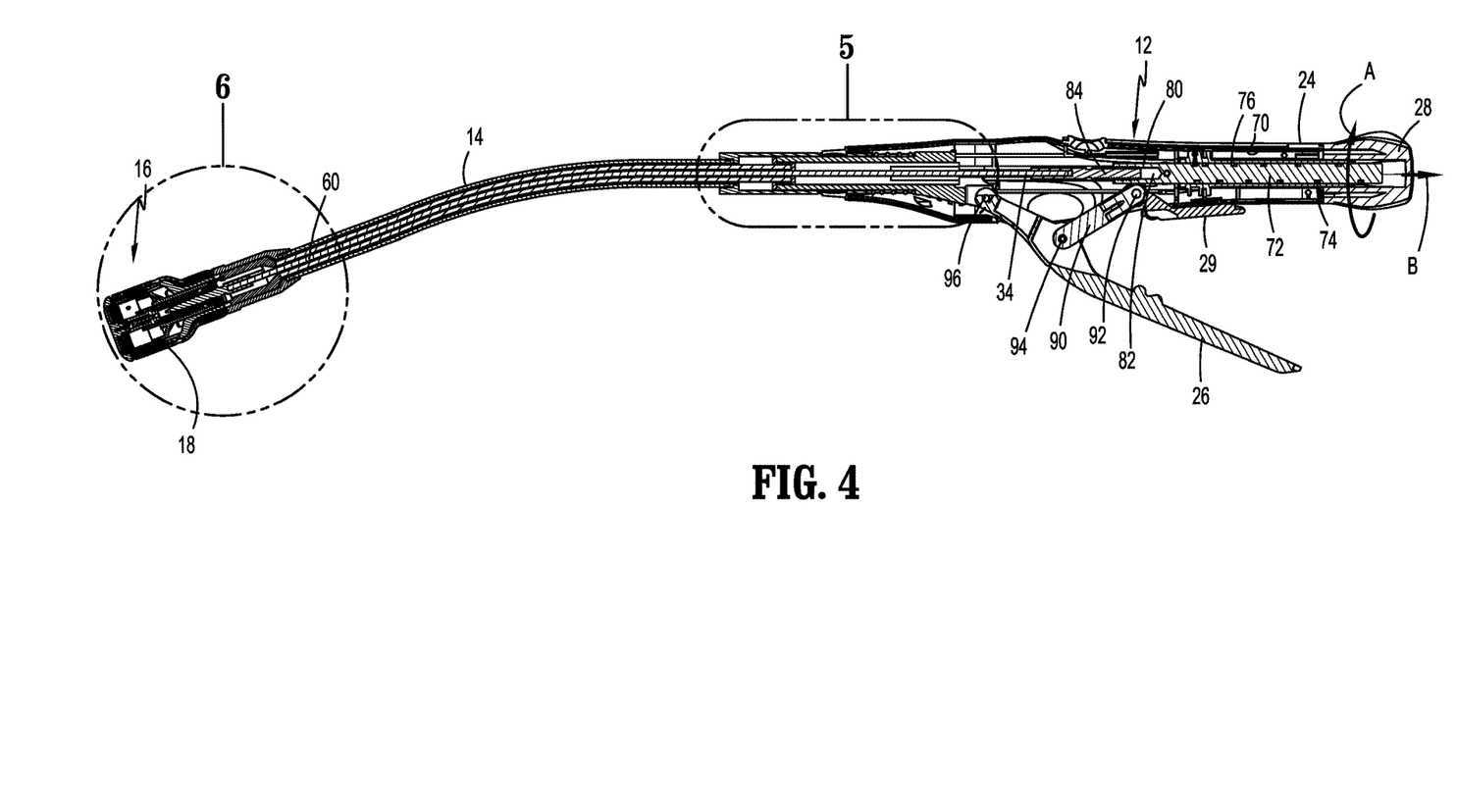
FIG. 4 is a cross-sectional view taken along section line 4-4 of FIG. 1 with the tool assembly in the clamped position.

FIG. 1 illustrates a circular stapling device shown generally as stapling device 10 including exemplary aspects of the disclosure. The stapling device 10 includes a handle assembly 12, an elongate body 14, and a tool assembly 16. The tool assembly 16 includes a reload or shell assembly 18, and an anvil assembly 20 that is supported for movement in relation to the reload assembly 18 between open and clamped positions. In aspects of the disclosure, the reload assembly 18 includes a housing 22 having proximal coupling portion 22a that is releasably coupled to a distal portion 14a of the elongate body 14 to facilitate replacement of the reload assembly 18 and reuse of the stapling device 10. Alternately, the reload assembly 18 can be fixedly secured to the distal portion of the elongate body 14. The handle assembly 12 includes a stationary handle 24 and a trigger 26 that can pivot towards the stationary handle 24 to fire staples from the reload assembly 18 into the anvil assembly 20 as described in further detail below. The stationary handle 24 also supports a rotation knob 28 and a lockout member 29. The rotation knob 28 is provided to effect movement of the anvil assembly 20 in relation to the reload assembly 18 between open and clamped positions. The lockout member 29 is provided to prevent firing of the stapling device 10 until the anvil assembly 20 is moved to the clamped position (FIG. 4). U.S. Pat. No. 6,945,444 ("the '444 Patent") discloses a handle assembly that includes a suitable rotation knob and a lockout member.

Figure 2:
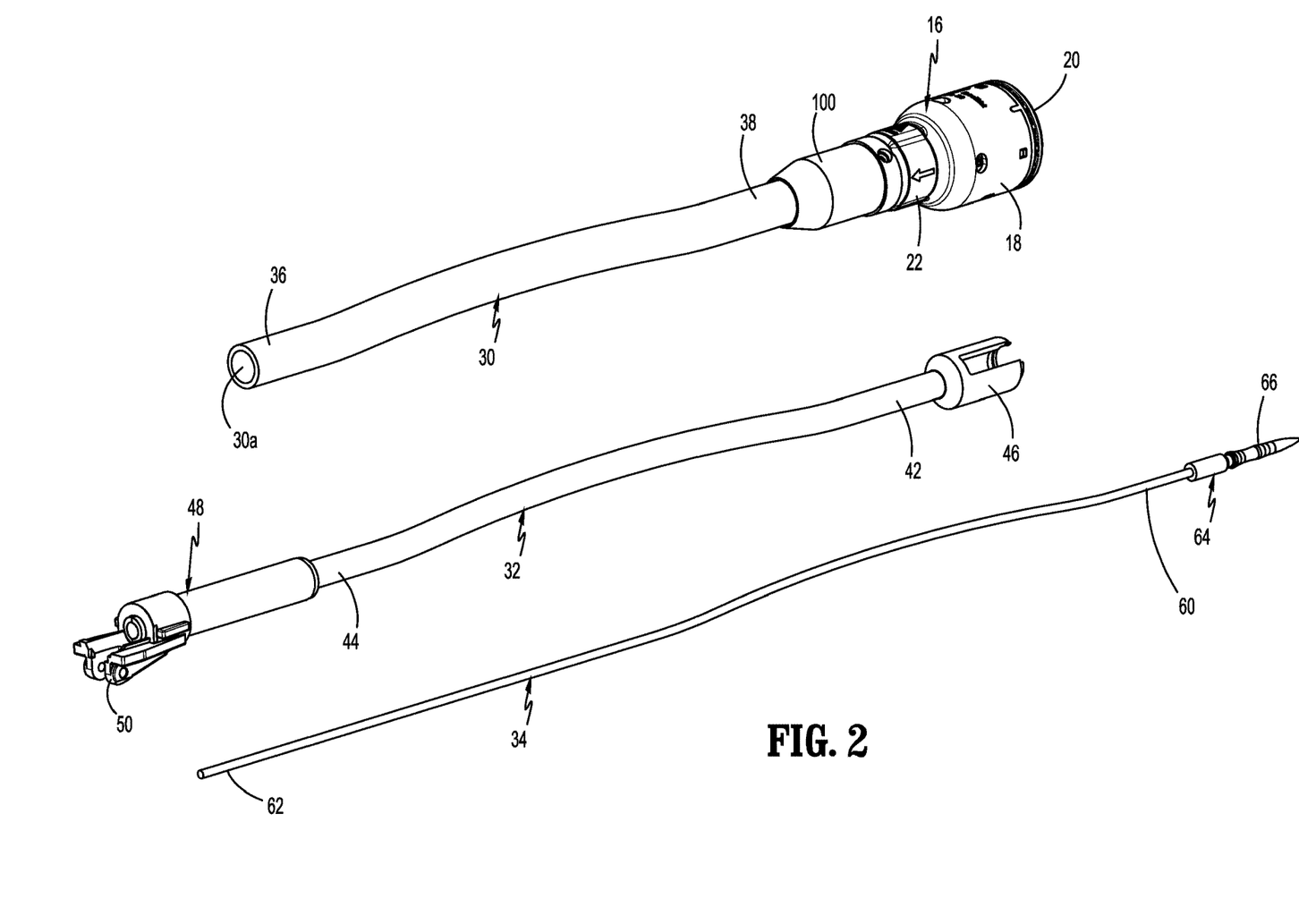
FIG. 2 is a partially exploded, perspective view of a distal portion of the surgical stapling device shown in FIG. 1.

FIG. 2 illustrates an exploded view of the elongate body 14 of the stapling device 10 with the tool assembly 16 of the stapling device 10 secured to an outer tube 30 of the elongate body 14. The elongate body 14 includes the outer tube 30, a central tube 32, and an inner cable 34. The outer tube 30 has a proximal portion 36 and a distal portion 38. The outer tube 30 defines a central through bore 30a. The distal portion 38 of the outer tube 30 releasably engages the proximal coupling portion 22a of the body 22 of the reload assembly 18 to secure the body 22 of the reload assembly 18 at a fixed axial position on the distal portion 38 of the outer tube 30. See, e.g., U.S. Pat. No. 10,085,744 for a detailed description of a coupling portion for securing a reload assembly to a body of a stapling device. The proximal end 36 of the outer tube 30 is fixedly secured to the handle assembly 12 of the stapling device 10. In some aspects of the disclosure, the proximal end 36 of the outer tube 30 is received within a rigid tubular member 40 (FIG. 3) that is secured to the handle assembly 12. In aspects of the disclosure, the outer tube 30 is formed from a flexible material such as a material formed from rubber, urethane, polytetrafluoroethylene (PTFE), polyether ether ketone (PEEK), anodized aluminum, stainless steel, titanium, gold, silver, etc. The outer tube 30 can also be formed of a plastic material with a metal stiffener to hold its shape. It is further envisioned that the outer tube 30 can be formed of nylon plastic flexible tubing. The outer tube 30 could also be formed from a malleable material such as any annealed or "dead soft" material.

The central tube 32 of the stapling device 10 defines a through bore 32a (FIG. 5), is received within the central through bore 30a of the outer tube 30 and is movable in response to actuation of the trigger 26 between retracted and advanced positions. The central tube 32 includes a distal portion 42 and a proximal portion 44. The distal portion 42 of the central tube 32 is secured to a drive member 46 that is received within the body 22 of the reload assembly 18. The proximal portion 44 of the central tube 32 is secured to a coupling member 48. The coupling member 48 includes a yoke 50 that is coupled to the trigger 26 (FIG. 3) as described below. In aspects of the disclosure, the coupling member 48 and the drive member 46 are formed of substantially rigid materials such as polyethylene, and the central tube 32 is formed from a flexible material. In aspects of the disclosure, the central tube 32 is formed of coil pipe, e.g., polyethylene coil pipe that can withstand compression.

The inner cable 34 is received within the central through bore 32a of the central tube 32 and includes a distal portion 60 and a proximal portion 62. The distal portion 60 of the inner cable 34 is secured to an anvil retainer 64 which is in the form of a trocar 66. The trocar 66 is configured to releasably engage the anvil assembly 20 (FIG. 1). The '444 Patent discloses an anvil retainer including a trocar and an anvil assembly that is releasably coupled to the trocar. The proximal portion 62 of the inner cable 34 extends into the handle assembly 12 (FIG. 1) through a spacer 67 (FIG. 5) positioned within the coupling member 48 and is coupled to the rotation knob 28 as described below. In aspects of the disclosure, the inner cable 34 is formed from a flexible material that can withstand tension such as wire rope.

Figure 3:
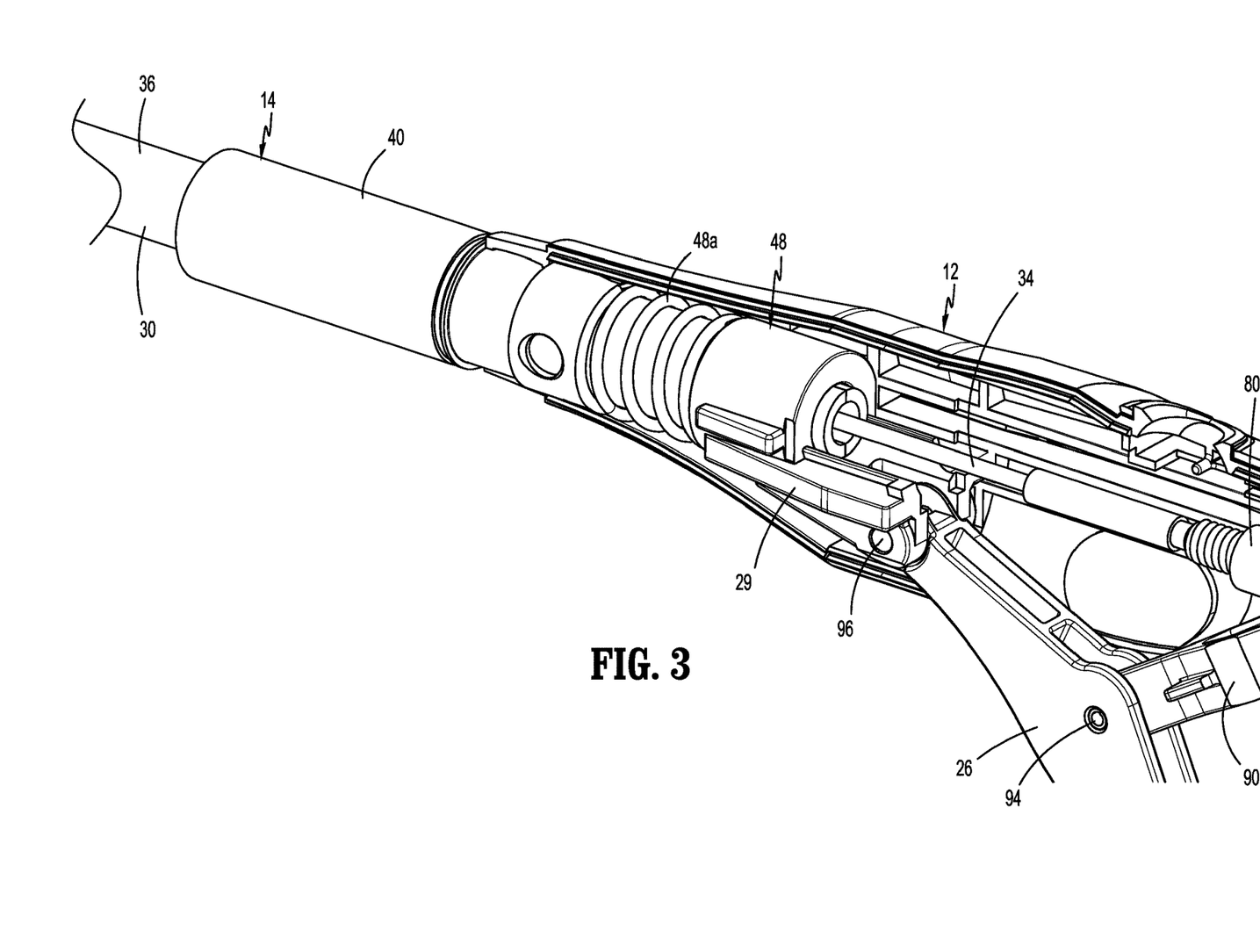
FIG. 3 is a side perspective view of a proximal portion of the surgical stapling device shown in FIG. 1 with a half-section of a housing of a handle assembly removed.
Figure 5:
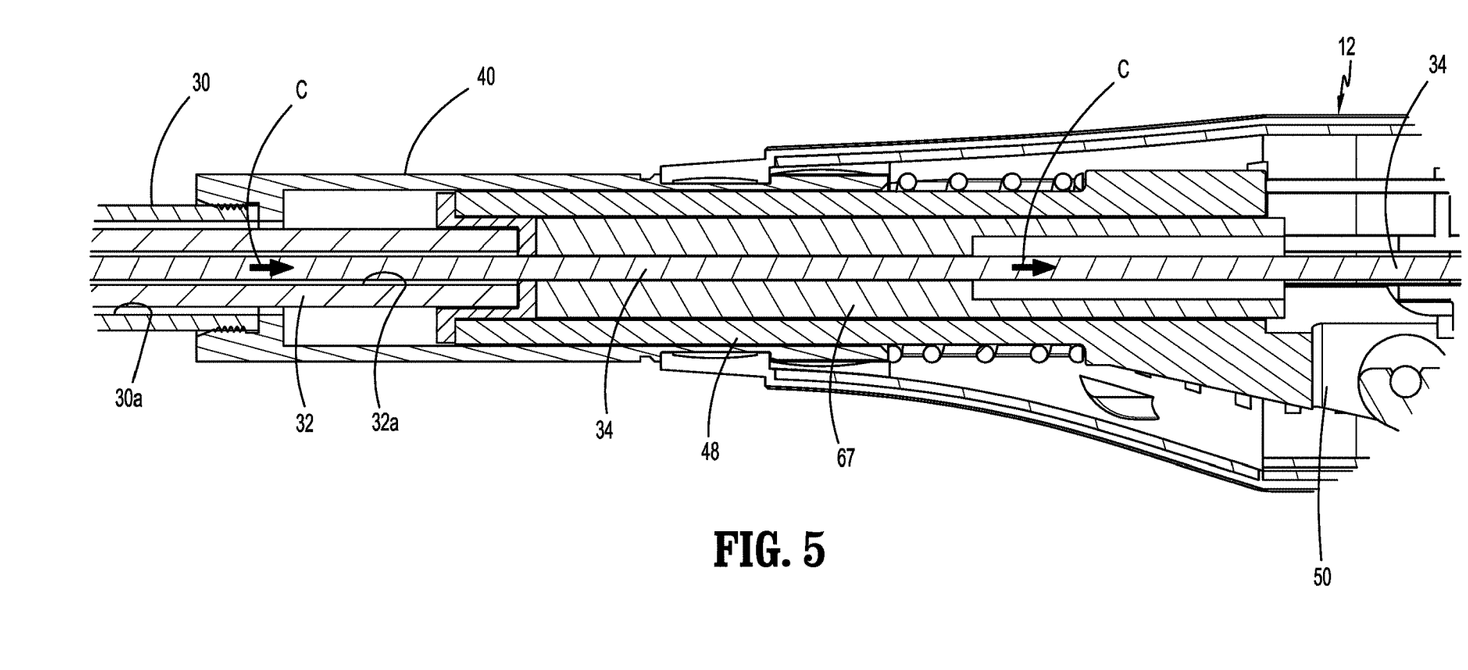
FIG. 5 is an enlarged view of the indicated area of detail shown in FIG. 4.

FIGS. 3-5 illustrate the interconnection between the handle assembly 12 and the elongate body 14 of the stapling device 10. The stationary handle 24 of the handle assembly 12 defines a cavity 70 that includes a screw 72 that defines a helical channel 74 (FIG. 4). The screw 72 is received in a tubular member 76 that is coupled to the rotation knob 28 such that rotation of the rotation knob 28 causes corresponding rotation of the tubular member 76 about the screw 72. The tubular member 76 is axially fixed in relation to the stationary handle 24 of the handle assembly 12 and supports a cam member (not shown) that is received in the helical channel 74. When the rotation knob 28 is rotated in relation to the stationary handle 24 to rotate the tubular member 76 about the screw 72, movement of the cam member (not shown) within the helical channel 74 causes longitudinal movement of the screw 72 within the stationary handle 24.

The screw 72 is has a distal portion 80 that defines a bore 82 that receives a connector 84 (FIG. 4) that has a proximal portion that is coupled to the screw 72 and a distal portion that is coupled to the inner cable 34. As described above, the inner cable 34 has a distal portion 60 that is coupled to the anvil retainer 64 and trocar 66. When the screw 72 is moved longitudinally within the stationary handle 24 by actuation of the rotation knob 28 to move the screw 72 between its advanced and retracted positions, the inner cable 34 is moved from an advanced position to a retracted position to move the anvil assembly 20 in relation to the body 22 of the reload assembly 18 from the open position (FIG. 1) to the clamped position (FIG. 6).

The trigger 26 is coupled to the stationary handle 24 by a link 90. The link 90 has a first end that is pivotably coupled to the stationary handle 24 by a pivot member 92 and a second end that is pivotably coupled to the trigger 26 by a pivot member 94. The trigger 26 has a distal portion that is coupled to the yoke 50 of the coupling member 48 by a pivot member 96 (FIG. 3). The coupling member 48 is secured to the central tube 32 such that when the trigger 26 is pivoted towards the stationary handle 24, the link 90 moves the trigger 26 distally to advance the coupling member 48 and the central tube 32 distally within the outer tube 30 and advance the drive member 46 in relation to the body 22 of the reload assembly 18. In aspects of the disclosure, the coupling member 48 can be secured to the central tube by pressing, pinning, gluing or the like. A biasing member, e.g., a coil spring 48a (FIG. 3), can be provided to urge the coupling member 48 and the central tube 32 to their retracted positions.

Figure 6:
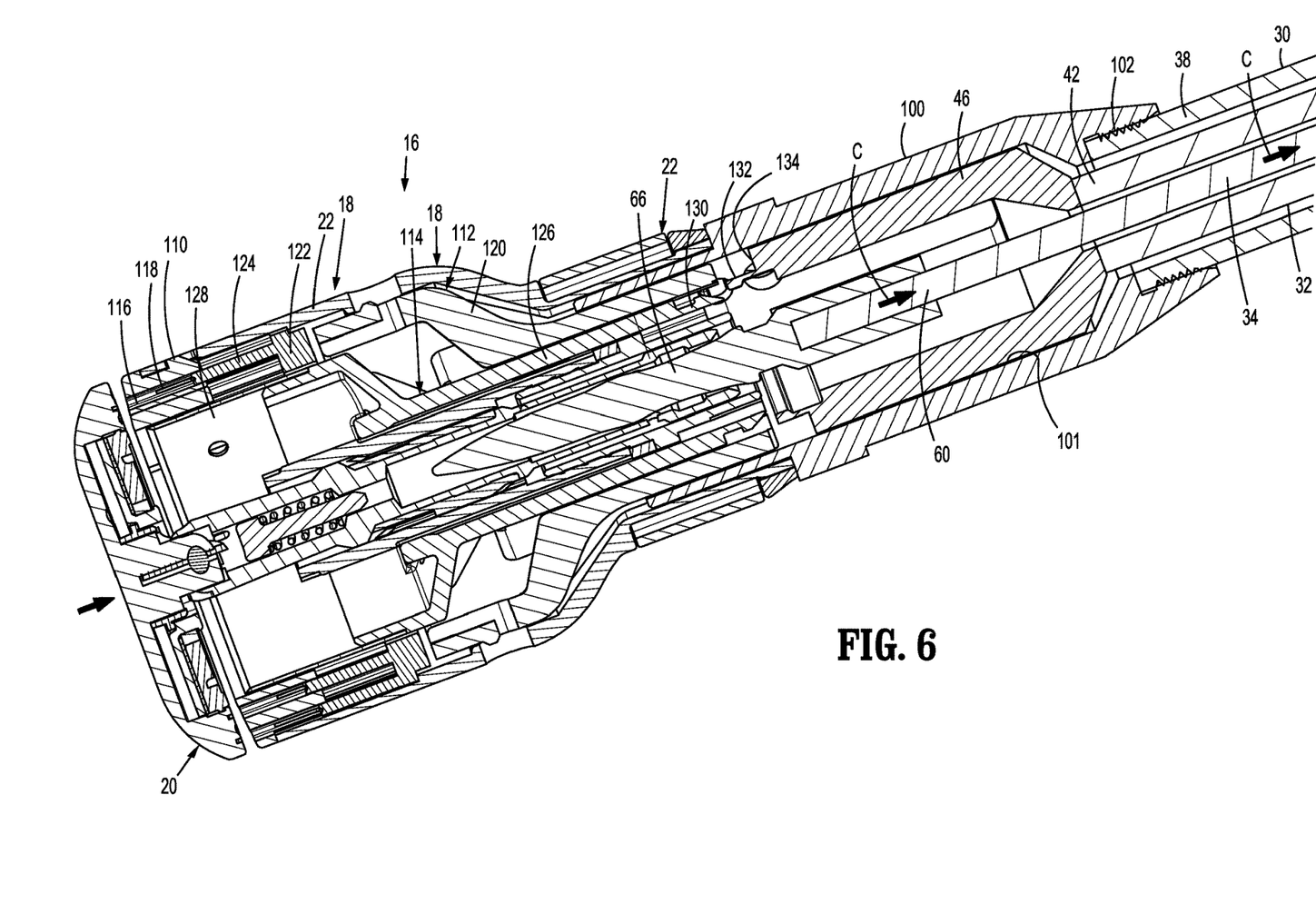
FIG. 6 is an enlarged view of the indicated area of detail shown in FIG. 4.

FIG. 6 illustrates the interconnection between the elongate body 14 and the reload assembly 18. The distal portion 38 of the outer tube 30 is coupled to a substantially rigid connector 100. In aspects of the disclosure, the connector 100 defines a cavity 101 and includes a distal portion and a proximal portion. The proximal portion of the connector 100 is coupled to the distal portion 38 of the outer tube 30 by threads 102 to axially fix the connector 100 to the outer tube 30. The distal portion of the connector 100 is adapted to be releasably coupled to the body 22 of the reload assembly 18 via the coupling assembly 22a of the reload assembly 18.

The drive member 46 which is supported on the distal portion 42 of the central tube 32 is received within the cavity 101 of the connector 100 and is movable within the cavity 101 between retracted and advanced positions. The reload assembly 18 includes an annular staple cartridge 110, a pusher assembly 112, and a knife assembly 114. The staple cartridge 110 defines an annular array of staple receiving slots 116. Each of the staple receiving slots 116 receives a staple 118. The pusher assembly 112 includes a pusher body 120 and a staple pusher 122. The staple pusher 122 includes fingers 124 that are received within the staple receiving slots 116 of the staple cartridge 110. The knife assembly 114 include a knife support 126 that supports an annular knife blade 128. A proximal portion of the knife support 126 includes first coupling structure 130.

The distal portion of the drive member 46 includes second coupling structure 132 and an abutment 134. The abutment 134 is aligned with a proximal end of the pusher body 120 and the pusher body 120 is in abutting relation to the staple pusher 122. When the drive member 46 is moved within the cavity 101 of the connector 100 from its retracted position to its advanced position, the pusher body 120 and the staple pusher 122 are advanced within the body 22 of the reload assembly 18 to move the fingers 124 of the staple pusher 122 through the staple receiving slots 116 of the staple cartridge 110 to eject the staples 118 from the staple receiving slots 116 of the staple cartridge 110.

The second coupling structure 132 of the drive member 46 is aligned with the first coupling structure 130 of the knife support 126 of the knife assembly 114. When the drive member 46 is moved within the cavity 101 of the connector 100, the drive member 46 engages and is coupled to the knife support 126. Further movement of the drive member 46 moves the knife support 126 distally within the body 22 of the reload assembly 118 to advance the annular knife blade 128 through the staple cartridge 110 and into engagement with the anvil assembly 18 to cut tissue clamped between the anvil assembly 18 and the staple cartridge 110. Because the drive member 46 is engaged with the knife support 126 via the first and second coupling structures 130 and 132, respectively, retraction of the drive member 46 withdraws the annular knife blade 128 back to a position within the body 22 of the reload assembly 18. It is noted that the coil spring 48a (FIG. 3) returns the knife support 126, the knife blade 128, the drive member 46, and the central tube 32 to their retracted positions when the clinician releases the trigger 26.

FIGS. 4-6 illustrate the stapling device 10 as the anvil assembly 20 is moved from the spaced position (FIG. 1) towards the clamped position (FIG. 6). When the rotation knob 28 (FIG. 4) is rotated in the direction indicated by arrow "A" in FIG. 4, the screw 72 is retracted in the direction of arrow "B". The screw 72 is coupled to the inner cable 34 by the connector 84 such that retraction of the screw 72 causes the inner cable 34 to retract or move proximally in the direction indicated by arrows "C" in FIG. 5 within the central tube 32. As the inner cable 34 moves proximally within the central tube 32, the anvil assembly 20 which is supported on the trocar 66 (FIG. 6) secured to the distal portion 60 of the inner cable 32 is moved proximally towards the staple cartridge 110 to the clamped position (FIG. 6). The outer tube 30 which is fixedly secured to the reload 18 and to the handle assembly 12 is sufficiently rigid to facilitate clamping of tissue between the anvil assembly 20 and the staple cartridge 110.

Figure 7:
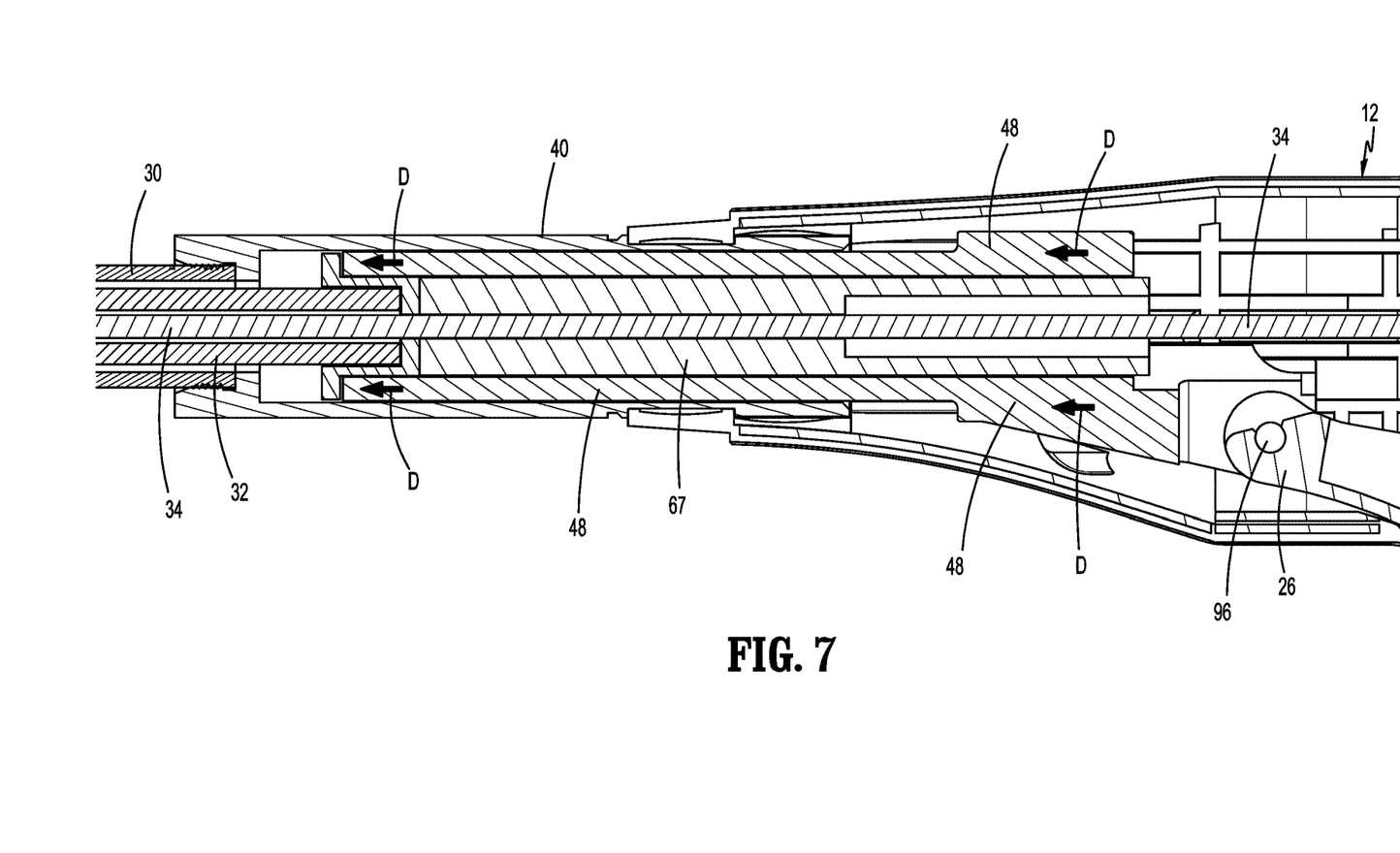
FIG. 7 is a side cross-sectional view of the indicated area of detail shown in FIG. 5 as the surgical stapling device is moved to the fired position.
Figure 8:
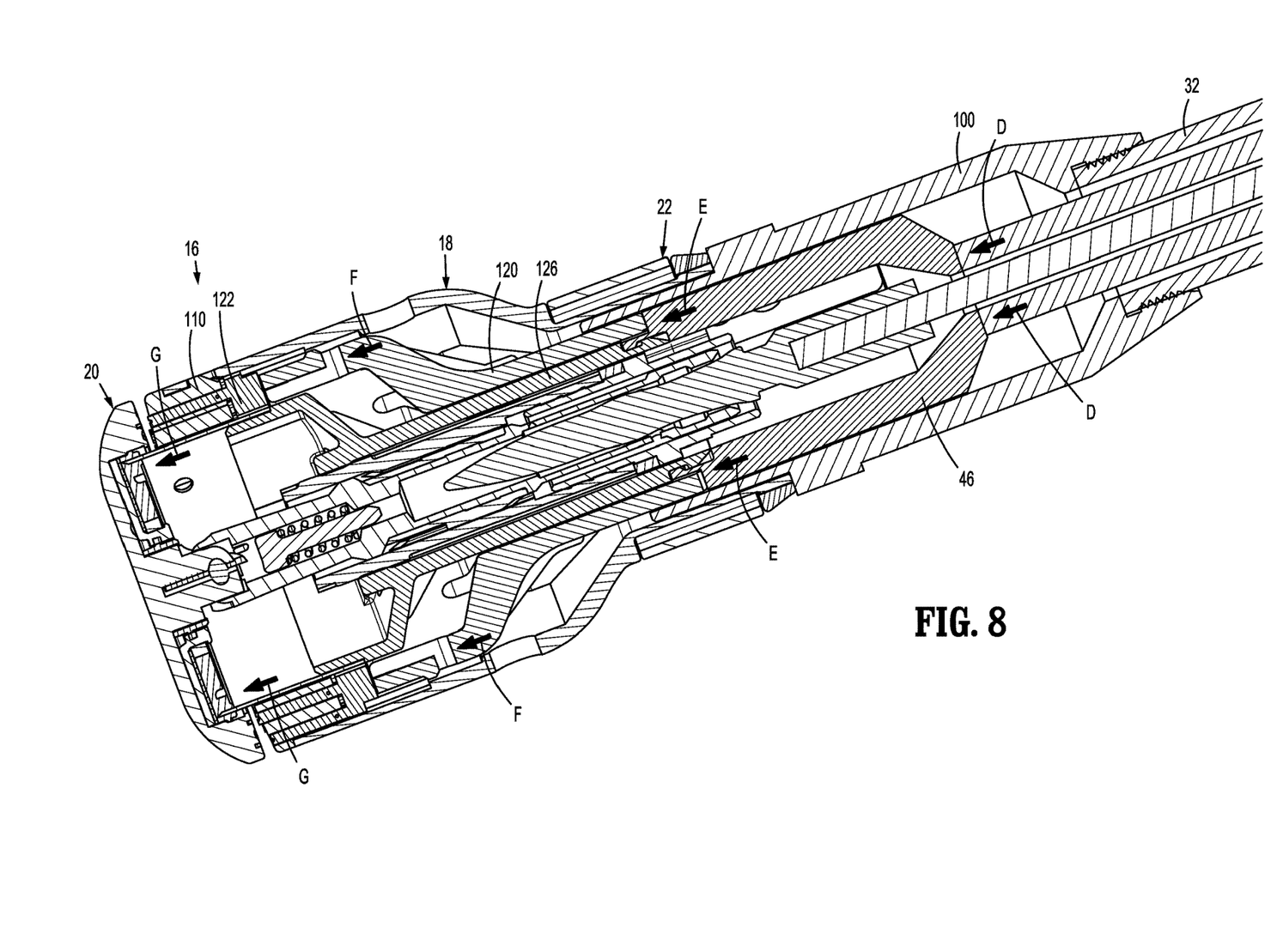
FIG. 8 is a side cross-sectional view of the indicated area of detail shown in FIG. 6 as the surgical stapling device is moved to the fired position.

FIGS. 7 and 8 illustrate the stapling device 10 as the stapling device 10 is fired. When the trigger 26 of the handle assembly 12 is compressed towards the stationary handle 24, the trigger 26 pivots in a distal direction to move coupling member 48 (which is secured to the proximal portion 44 of the central tube 32) and the central tube 32 distally within the outer tube 30 in the direction of arrows "D". Distal movement of the central tube 32 within the outer tube 30 causes the drive member 46 to move within the cavity 101 of the connector 100 in the direction of arrows "E" in FIG. 8 to move the pusher body 120 and the knife support 126 distally in the direction of arrows "F" in FIG. 8. Distal movement of the pusher body 120 causes the staple pusher 122 to move distally in the direction of arrows "G" in FIG. 8 to eject staples 118 (FIG. 6) from the staple cartridge 110. Similarly, distal movement of the knife support 126 causes distal movement of the annular knife blade 128 in the direction of arrows "G" through the annular staple cartridge 110 to remove tissue from within the staple cartridge 110.

When the stapling device 10 is actuated to move the anvil assembly 20 from the spaced position (FIG. 1) towards the clamped position (FIG. 8), the outer tube 30 is in compression and the inner cable 34 is in tension. The central tube 32 is positioned about the inner cable 34 and within the outer tube 30 to provide support to these components. When the stapling device 10 is actuated to fire staples from the staple cartridge 110, the central tube 32 is in compression and is supported between the inner cable 34 and the outer tube 30.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A surgical stapling device comprising:
a handle assembly including a stationary handle, a trigger coupled to the stationary handle, and a rotation knob;
an elongate body including a flexible outer tube, a flexible central tube, and a flexible inner cable, the flexible outer tube having a proximal portion and a distal portion, the proximal portion of the flexible outer tube fixedly coupled to the stationary handle of the handle assembly, the flexible central tube having a proximal portion and a distal portion and movable within the flexible outer tube between retracted and advanced positions, the proximal portion of the flexible central tube coupled to the trigger of the handle assembly such that actuation of the trigger causes movement of the flexible central tube between its retracted and advanced positions, the flexible inner cable movable within the central tube between advanced and retracted positions and including a proximal portion and a distal portion, the distal portion of the flexible central tube supporting an anvil retainer, the proximal portion of the flexible inner cable coupled to the rotation knob such that rotation of the rotation knob in relation to the stationary housing of the handle assembly causes movement of the flexible inner cable between its retracted and its advanced positions; and a tool assembly including:
- a reload assembly supported on the distal portion of the outer tube, the reload assembly including a body supporting a staple cartridge having staples; and
- an anvil assembly coupled to the anvil retainer, the anvil assembly being movable in relation to the staple cartridge between spaced and clamped positions in response to movement of the flexible inner cable between its advanced and retracted positions.

2. The surgical stapling device of claim 1, wherein the anvil retainer includes a trocar and the anvil assembly is adapted to be releasably coupled to the trocar.

3. The surgical stapling device of claim 1, wherein the distal portion of the flexible outer tube is coupled to the body of the reload assembly by a rigid connector, the rigid connector defining a cavity.

4. The surgical stapling device of claim 3, wherein the distal portion of the flexible central tube includes a rigid drive member, the rigid drive member movable within the cavity of the connector between retracted and advanced positions in response to movement of the flexible central tube between its retracted and advanced positions.

5. The surgical stapling device of claim 4, wherein the reload assembly includes a pusher assembly, the pusher assembly movable from a retracted position to an advanced position in response to movement of the drive member from its retracted to its advanced position to eject the staples from the staple cartridge.

6. The surgical stapling device of claim 5, wherein the reload assembly includes a knife assembly including an annular knife blade, the knife assembly movable from a retracted position to an advanced position in response to movement of the drive member from its retracted position to its advanced position to advance the annular knife blade through the staple cartridge.

7. The surgical stapling device of claim 1, wherein the proximal portion of the central tube supports a rigid coupling member that is coupled to the trigger by a pivot member.

8. The surgical stapling device of claim 3, wherein the reload assembly is releasably coupled to the body of the reload assembly by a coupling mechanism.

9. The surgical stapling device of claim 1, wherein the flexible central tube is formed from coil pipe.

10. The surgical stapling device of claim 1, wherein the inner cable is formed from wire rope.

11. The surgical stapling device of claim 1, wherein the outer tube is formed from nylon plastic flexible tubing.

12. The surgical stapling device of claim 1, wherein the inner cable is formed from wire rope, the flexible central tube is formed from coil pipe, and the outer tube is formed from flexible tubing.

13. A surgical stapling device comprising:
a handle assembly including a stationary handle, a trigger coupled to the stationary handle, and a rotation knob;
an elongate body including a flexible outer tube, a flexible central tube, and a flexible inner cable, the flexible outer tube having a proximal portion and a distal portion, the proximal portion of the flexible outer tube fixedly coupled to the stationary handle of the handle assembly, the flexible central tube having a proximal portion and a distal portion and movable within the flexible outer tube between retracted and advanced positions, the proximal portion of the flexible central tube coupled to the trigger of the handle assembly such that actuation of the trigger causes movement of the flexible central tube between its retracted and advanced positions, the flexible inner cable movable within the central tube between advanced and retracted positions and including a proximal portion and a distal portion, the distal portion of the flexible inner cable supporting an anvil retainer, the proximal portion of the flexible inner cable coupled to the rotation knob such that rotation of the rotation knob in relation to the stationary housing of the handle assembly causes movement of the flexible inner cable between its retracted and its advanced positions;

a tool assembly including:
- a reload assembly supported on the distal portion of the outer tube, the reload assembly including a body supporting a staple cartridge having staples; and
- an anvil assembly coupled to the anvil retainer, the anvil assembly being movable in relation to the staple cartridge between spaced and clamped positions in response to movement of the flexible inner cable between its advanced and retracted positions;

a rigid connector defining a cavity connecting the flexible outer tube to the body of the reload assembly, the rigid connector defining a cavity; and a rigid drive member supported on the distal portion of the flexible central tube, the rigid drive member movable within the cavity of the connector between retracted and advanced positions in response to movement of the flexible central tube between its retracted and advanced positions.

14. The surgical stapling device of claim 13, wherein the inner cable is formed from wire rope, the flexible central tube is formed from coil pipe, and the outer tube is formed from flexible tubing.

15. The surgical stapling device of claim 14, wherein the reload assembly includes a pusher assembly, the pusher assembly movable from a retracted position to an advanced position in response to movement of the drive member from its retracted to its advanced position to eject the staples from the staple cartridge.

16. The surgical stapling device of claim 15, wherein the reload assembly includes a knife assembly including an annular knife blade, the knife assembly movable from a retracted position to an advanced position in response to movement of the drive member from its retracted position to its advanced position to advance the annular knife blade through the staple cartridge.

17. The surgical stapling device of claim 13, wherein the anvil retainer includes a trocar and the anvil assembly is adapted to be releasably coupled to the trocar.

18. A surgical stapling device comprising:
a handle assembly including a stationary handle, a trigger coupled to the stationary handle, and a rotation knob;
an elongate body including an outer tube formed of flexible tubing, a central tube formed of coil pipe, and an inner cable formed of wire rope, the outer tube having a proximal portion and a distal portion, the proximal portion of the outer tube fixedly coupled to the stationary handle of the handle assembly, the central tube having a proximal portion and a distal portion and movable within the outer tube between retracted and advanced positions, the proximal portion of the central tube coupled to the trigger of the handle assembly such that actuation of the trigger causes movement of the central tube between its retracted and advanced positions, the inner cable movable within the central tube between advanced and retracted positions and including a proximal portion and a distal portion, the distal portion supporting an anvil retainer, the proximal portion of the inner cable coupled to the rotation knob such that rotation of the rotation knob in relation to the stationary housing of the handle assembly causes movement of the inner cable between its retracted and its advanced positions; and a tool assembly including:
  a reload assembly supported on the distal portion of the outer tube, the reload assembly including a body supporting a staple cartridge having staples; and
  an anvil assembly coupled to the anvil retainer, the anvil assembly movable in relation to the staple cartridge between spaced and clamped positions in response to movement of the inner cable between its advanced and retracted positions.

19. The surgical stapling device of claim 18, wherein the anvil retainer includes a trocar and the anvil assembly is adapted to be releasably coupled to the trocar.

20. The surgical stapling device of claim 18, wherein the distal portion of the flexible outer tube is coupled to the body of the reload assembly by a rigid connector, the rigid connector defining a cavity, and the distal portion of the flexible central tube includes a rigid drive member, the rigid drive member movable within the cavity of the connector between retracted and advanced positions in response to movement of the flexible central tube between its retracted and advanced positions.

* * * * *